though a United States Patent [19]

Bowman

[11] 4,042,701
[45] Aug. 16, 1977

[54] 7,7-DIPHENYL-1,4-OXAZEPINOALKYL-DICARBOXIMIDES

[75] Inventor: Robert Mathews Bowman, Summit, N.J.

[73] Assignee: Ciba-Geigy Corporation, Ardsley, N.Y.

[21] Appl. No.: 615,259

[22] Filed: Sept. 22, 1975

[51] Int. Cl.$^2$ .............................................. C07D 413/6
[52] U.S. Cl. .................... 424/267; 424/274;
424/244; 260/239.3 R; 260/281 GN; 260/326
N; 260/326.5 FM; 260/333
[58] Field of Search ................. 260/239.3 R, 281 GN,
260/326 N, 326.5 FM; 424/267, 274, 244

[56] References Cited
U.S. PATENT DOCUMENTS

| 3,081,308 | 3/1963 | Kalm | 260/281 GN |
| 3,106,552 | 10/1963 | Grogan et al. | 260/326.5 FM |
| 3,410,842 | 11/1968 | Allais et al. | 260/239.3 R |

Primary Examiner—Henry R. Jiles
Assistant Examiner—Robert T. Bond
Attorney, Agent, or Firm—Joseph G. Kolodny; Theodore O. Groeger; John J. Maitner

[57] ABSTRACT

N-(7,7-Diphenyl-hexahydro-1,4-oxazepin-4-yl-alkyl)-dicarboximides, e.g. those of the formula:

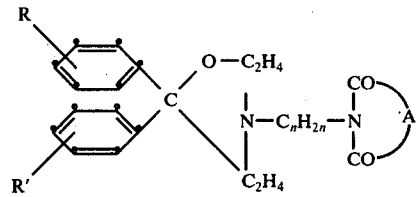

A = aliphatic, cycloaliphatic or aromatic radical
R,R' = H, alkyl, OH, alkoxy, alkyl-mercapto, halogen or CF$_3$
n = 2-4 and acid addition salts thereof are antiasthmatics.

8 Claims, No Drawings

7,7-DIPHENYL-1,4-OXAZEPINOALKYL-DICARBOXIMIDES

SUMMARY OF THE INVENTION

The present invention concerns and has for its object the provision of new N-(7,7-diphenyl-hexahydro-1,4-oxazepin-4-ylalkyl)-dicarboximides, more particularly of those of Formula I

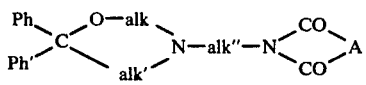

wherein each of alk and alk' is lower alkylene separating the adjacent atoms by 2 carbon atoms, alk" is lower alkylene separating the adjacent atoms by at least 2 carbon atoms, each of Ph and Ph' is phenyl, unsubstituted or substituted by up to three members of lower alkyl, alkoxy, alkylmercapto, hydroxy, halogeno or trifluoromethyl, and A is lower alkylene, alkenylene, mono- or bicycloalkylene or -alkenylene, spirocycloalkane-alkylene or 1,2-phenylene, unsubstituted or the aliphatic radicals substituted by up to three lower alkyls, and the phenyl radical substituted as Ph, or a therapeutically acceptable acid addition salt thereof; of corresponding pharmaceutical compositions and of methods for the preparation and application of these products, which are useful antiasthmatic, antiallergic and antiinflammatory agents.

DESCRIPTION OF THE PREFERRED EMBODIMENTS

A lower alkylene group alk, alk' and alk" is preferably ethylene, but also, for example 1,2-propylene or -butylene. The group alk" also represents 1,3-propylene or -butylene or 1,4-butylene. The term "lower" referred to above or hereinafter in connection with organic radicals or compounds respectively defines such with up to 7, preferably up to 4 carbon atoms.

Of the radicals Ph and Ph' one is preferably phenyl and the other phenyl, (lower alkyl)-phenyl, mono-, di- or tri-(lower alkoxy)-phenyl, (lower alkylmercapto, hydroxy, halogeno or trifluoromethyl)-phenyl, wherein alkyl preferably represents methyl, but also ethyl, n- or i-propyl or -butyl, lower alkoxy or alkylmercapto are preferably methoxy or methylmercapto, but also ethoxy, n- or i-propoxy or -butoxy, or ethylmercapto respectively, and halogeno is preferably fluoro, chloro or bromo.

A lower alkylene or alkenylene radical A is preferably ethylene, 1,3-propylene, 2,2-di-(methyl, ethyl, n-propyl or n-butyl)-1,3-propylene, 1,4-butylene or 1,4-but-2-enylene.

A mono- or bicycloalkylene or -alkenylene radical is preferably 5 to 7 ring-membered and unsubstituted, or substituted by up to 3 lower alkyls, preferably methyls, such as 1,2- or 1,3-cyclopentylene or -cyclohexylene, 1,2,2-trimethyl-1,3-cyclopentylene, 2-methyl-1,3-cyclohexylene, 3,6-ethano-1,2-cyclohexylene or -cyclo-4-hexenylene.

A spirocycloalkane-alkylene radical A is preferably a 5 to 7 ring-membered unsubstituted 2-spirocycloalkane-1,3-propylene group, e.g. 2-spirocyclopentane- or -hexane-1,3-propylene or such radicals alkylated as shown above.

A 1,2-phenylene radical A is preferably unsubstituted or substituted as shown for the phenyl radicals Ph and Ph'.

The acid addition salts of the compounds of Formula I are preferably derived from the therapeutically acceptable acids listed below.

The compounds of the invention exhibit valuable pharmacological properties, for example, antiasthmatic, antiallergic and antiinflammatory effects. This can be demonstrated either in vitro or in vivo tests, using advantageously mammals, such as mice, rats, guinea pigs or dogs as test objects, or isolated organs thereof. The in vitro tests are performed either with human leukocytes of volunteers who are allergic to ragweed pollen, or with the guinea pig ileum in a standard organ bath, e.g. physiological saline. In the former test, as described by Lichtenstein et al, J. Exp. Med. 120, 507 (1964), the aqueous leukocyte suspension, when treated with a purified ragweed pollen extract (antigen E), releases histamine, which can be estimated fluorometrically. The compounds of the invention, especially the N-[3-(7,7-diphenylhexahydro -1,4-oxazepin-4-yl)-propyl]-$\beta$,$\beta$-tetramethylene-giutarimide hydrochloride, being illustrative thereof, when added to said leukocyte suspension, or ilium bath, in an amount to reach concentrations down to about $10^{-5}$ molar, inhibit the histamine release of the leukocytes, or the histamine-induced ileum-contraction respectively, thus indicating antiallergic and antihistaminic effects, which latter are also confirmed by the classical in vivo tests in mice, rats and guinea pigs. With enteral or parenteral, e.g. oral or intravenous, doses of said compounds, for example in the range between 0.1 and 200 mg/kg/day, preferably between about 1 and 100 mg/kg/day, especially with about 5 or 10 mg/kg/day i.v., or with about 50 or 100 mg/kg/day p.o. doses of said hydrochloride, significant protection against egg-albumin anaphylaxis, or passive cutaneous anaphylaxis is achieved (J. Carr, J. Path. 108, 1, 1972).

Antiasthmatic activity is estimated in dogs, who are naturally sensitive to ascaris antigens, causing asthma-like syndromes after inhalation of said nebulized antigens. The compounds of the invention are administered orally or intraveneously in about the same dosage ranges mentioned above, about 30 -60 minutes after antigen-challenge, and efficacy is observed by the change in the dogs' respiratory-rate and airway-resistance.

Accordingly, the compounds of the invention can be applied enterally or parenterally, e.g. by inhalation of a nebulized aqueous solution, or by peroral, subcutaneous, intramuscular or intraveneous administration, in about the dosage range shown above. According to the test results obtained, they are useful antiasthmatic, antiallergic and antihistaminic agents. They are also valuable intermediates of other preparations, preferably of pharmacologically useful products.

Particularly useful are compounds of Formula I, wherein each of alk and alk' is lower alkylene separating the adjacent atoms by 2 carbon atoms, alk" is lower alkylene separating the adjacent atoms by at least 2 carbon atoms, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, and A is lower alkylene, lower alkenylene,5 to 7 ring-membered mono- or bicyclic 1,2- or 1,3-cycloalkylene, -cycloalkenylene or 2-spirocycloalkane-1,3-propylene, 1,2-phenylene, (lower alkyl, lower alkoxy, lower alkylmercapto, hydroxy, halogeno or trifluoromethyl)-1,2-phenylene, or a therapeutically acceptable acid addition salt thereof.

Preferred compounds of the inventions are those of Formula I, wherein each of alk and alk' is ethylene or 1,2-propylene, alk" is ethylene, 1,3-propylene or 1,4-butylene, each of Ph and Ph' is phenyl or (lower alkyl)-phenyl, and A is ethylene, 1,3-propylene, 2,2-di-(methyl, ethyl, n-propyl or n-butyl)-1,2-propylene, 1,4-butylene or 1,4-but-2-enylene, 1,2- or 1,3-cyclopentylene or cyclohexylene, 1,2,2-trimethyl-1,3-cyclopentylene, 2-methyl-1,3-cyclohexylene, 3,6-ethano-1,2-cyclohexylene or -cyclo-4-hexenylene, 2-spirocyclopentane or -hexane-1,3-propylene, 1,2-phenylene or (lower alkyl)-1,2-phenylene, or a therapeutically acceptable acid addition salt thereof.

Outstanding on account of their usefulness are the compounds of Formula II

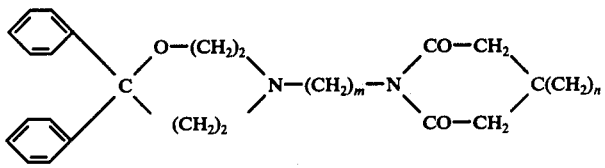

(II)

wherein m is an integer from 2 to 4 and n such from 4 to 5, or a therapeutically acceptable acid addition salt thereof.

The most preferred compounds are those of Formula II, wherein m is 3 or 4 and n is four, or a therapeutically acceptable acid addition salt thereof.

The compounds of this invention are prepared according to conventional methods, for example by condensing compounds of Formulae III and IV

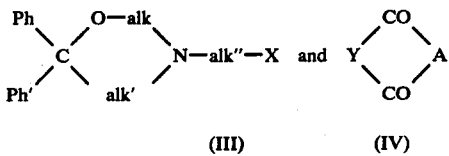

(III)            (IV)

wherein X is amino or reactively esterifield hydroxy and Y is oxygen or imino, or alkali metal salts thereof, provided that X + Y contain one nitrogen atom and, if desired, converting any resulting compound of Formula I into another compound of the invention.

A reactivity esterified hydroxy group X is preferably a halogen atom, advantageously chloro or bromo, or in aliphatic or aromatic sulfonyloxy group, such as alkane- or Ph-sulfonyloxy, e.g. mesyloxy, besyloxy, tosyloxy, closyloxy or brosyloxy; and an alkali metal salt is preferably the sodium or postassium salt of the compounds with Y=NH.

Said condensation either occurs spontaneously at room temperature or below, or under pyroyltic conditions, for example at temperatures between room temperature and about 200° and/or in the presence of agents removing the water or acids generated, such as azeotropic solvents, e.g. benzene, toluene or xylene, or alkali metal hydroxides, carbonates or bicarbonates; or tert. amines, e.g. tri-lower alkylamines, pyridine or lower alkylated-pyridines respectively.

In the compounds of Formula I so obtained, any olefinic A can be hydrogenated with catalytically activated hydrogen, e.g. hydrogen in the presence of palladium or platinum catalysts, or phenols obtained alkylated with said reactive esters of lower alkanols.

Finally, any resulting base can be converted into a corresponding acid addition salt, preferably with the use of a therapeutically useful acid or anion exchange preparation, or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or othes salts, for example, the picrates, can also be used for purification of the bases obtained; the bases are converted into salts, the salts are separated and the bases are librated from the salts. In view of the close relationship between the free compounds and the compounds in the form of their salts, whenever a compound is referred to in this context, a corresponding salt is also intended, provided such is possible or appropriate under the circumstances.

The starting material of Formula III can be prepared from the corresponding sec. amines of the formula

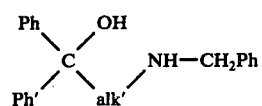

(described, together with the precursors, inter alia in J. Org. Chem. 33, 3402 (1968) or J. Chem. Soc. 1949, p.S. 144) by conventional acylation with said reactive derivatives of α-hydroxy-alkanoic acids, if desired by a following esterification of any diol obtained, e.g. with thionyl or phosphorus halides or oxyhalides or said sulfonic acids halides, and ring-closing the amides obtained, to form 4-benzyl-3-oxo-7,7-diphenyl-hexahydro-1,4-oxazepines. These are reduced with complex light metal hydrides, e.g. lithium aluminum hydride, and de-benzylated with catalytically activated hydrogen, to yield 4-unsubstituted 7,7-diphenyl-hexahydro-1,4-oxazepines. These in turn are condensed with reactive esters of hydroxy-alkanoic acid nitriles or alkane-diols (with different ester groups), and any nitrile obtained is reduced with said complex light metal hydrides to yield the compounds of Formula III. Those of Formula IV are well known dicarboxanhydrides or -imides.

In case mixtures of geometrical or optical isomers of the compounds of Formulae I to IV are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Thus, for example, the anhydrides IV may form with the amines III open amides first, which ring-close to the imides I or II by prolonged heating and/or azeotropic water-removal. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition they may also contain other therapeutically valuable substances. Said compositions are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centrigrade, and all parts wherever given are parts by weight. If not mentioned otherwise, all evaporations are performed under reduced pressure, preferably between about 15 and 100 mm Hg.

EXAMPLE 1

The mixture of 7.15 g of 4-(2-aminoethyl)-7,7-diphenylhexahydro-1,4-oxazepine, 4.05 g of $\beta,\beta$-tetramethylene-glutaric anhydride and 150 ml of xylene is stirred at reflux for 5 hours, during which time the liberated water is removed by a water trap. On cooling, the solution is washed with 2N aqueous sodium hydroxide and saturated aqueous sodium chloride, dried and evaporated. The residual solid is taken up in acetone, the solution treated with ethereal hydrogen chloride and the precipitate formed collected, to yield the N-[2-(7,7-diphenyl-hexahydro-1,4-oxazepin-4-yl)-ethyl]-$\beta,\beta$-tetramethylene-glutarimide hydrochloride of the formula

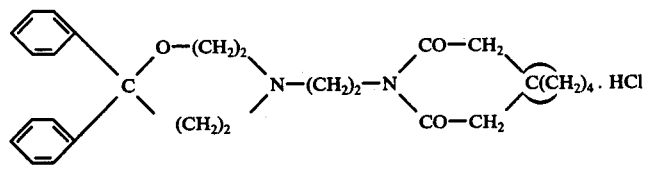

melting at 168°–170°.

The starting material is prepared as follows:

The solution of 8.2 g of acetonitrile in 200 ml of tetrahydrofuran is added dropwise to the solution of 14.08 g of butyl lithium in 125 ml of tetrahydrofuran and 125 ml of n-hexane while stirring at −70° under nitrogen and stirring is continued for 1 hour. Thereupon the solution of 36.4 g benzophenone in 200 ml o tetrahydrofuran is added dropwise and the mixture stirred for 20 minutes at room temperature. It is poured onto 300 g of ice and 100 ml of 3N hydrochloric acid, the organic layer separated and the aqueous phase extracted three times with 50 ml of diethyl ether. The combined organic solutions are dried, evaporated and the residue recrystallized from ethanol, to yield the $\beta$-hydroxy-$\beta$, $\beta$-diphenyl-propionitrile melting at 136°–138°.

35.5 g thereof are added portionwise to the stirred suspension of 12.9 g of lithium aluminum hydride in 80 ml of diethyl ether while cooling with an ice bath. After stirring for 15 hours at room temperature and 2 hours at the boil, it is cooled again and 12.9 ml of water, 12.9 ml of 15% aqueous sodium hydroxide and 38.7 ml of water are added in this order. The mixture is filtered, the residue washed 3 times with 150 ml of methylene chloride, the filtrate dried, evaporated and the residue recrystallized from ethanol, to yield the 3-hydroxy-3,3-diphenyl-propylamine melting at 134°–136°.

To the solution of 58.0 g thereof in 700 ml of methylene chloride and 30.5 g of pyridine, that of 37.5 g of benzoyl chloride in 300 ml of methylene chloride is added dropwise during 2 hours while stirring and cooling with an ice-bath. Stirring is continued for 1 hour at 0°14 5°, the mixture washed twice with 200 ml of N hydrochloric acid, 150 ml of 5% aqueous sodium hydroxide and 25 ml of water each, dried, evaporated and the residue triturated with diethyl ether, to yield the N-benzoyl-3-hydroxy-3,3-diphenylpropylamine melting at 140°-141°.

72.3 g thereof are added portionwise to the suspension of 16.3 g of lithium aluminum hydride in 1.6 lt of diethyl ether while stirring and cooling with an ice-bath. The mixture is stirred for 2 hours while warming to room temperature and 3 hours while refluxing. It is cooled again and 16.3 g of water, 16.3 ml of 15% aqueous sodium hydroxide and 49 ml water are added in this order, filtered and the residue washed 3 times with 300 ml of warm chloroform. The combined filtrates are dried and evaporated, to yield the N-benzyl-3-hydroxy-3,3-diphenylpropylamine melting at 145°-146°.

To the stirred solution of 15.6 g thereof in 7.0 g of di-isopropylethylamine and 150 ml of methylene chloride, that of 5.88 g of chloroacetyl chloride in 50 ml of methylene chloride is added dropwise while stirring and cooling with an ice-bath. Thereupon the solution is stirred for 15 minutes at 0°-5° and washed successively with N hydrochloric acid, 10% aqueous sodium bicarbonate and finally with saturated aqueous sodium chloride. The organic layer is separated, dried, filtered and evaporated, to yield the N-benzyl-N-chloroacetyl-3-hydroxy-3,3-diphenylpropylamine showing in the I.R.-spectrum a strong band at 1640 cm$^{-1}$.

The solution of 19.3 g thereof in 150 ml of dimethylformamide is added dropwise to the suspenson of 1.2 g of sodium hydride in 50 ml of dimethylformamide while stirring and cooling with an icebath. The mixture is allowed to warm up to room temperature, stirred for 15 hours and evaporated. The residue is partitioned between 150 ml methylene chloride and 50 ml of N hydrochloric acid, the organic layer separated, washed with water, dried, filtered and evaported. The residue is triturated with diethyl ether and recrystallized from ethanol, to yield the 4-benzyl-3-oxo-7,7-diphenyl-hexahydro-1,4-oxazepine melting at 185°-186°.

17.8 g thereof are added portionwise to the suspension of 2.28 g of lithium aluminum hydride in 300 ml of diethyl ether while stirring and cooling with an ice-bath. The mixture is allowed to warm up to room temperature and refluxed for 3½ hours. Then it is cooled with ice and 2.3 ml of water, 2.3 ml of 15% aqueous sodium hydroxide are added, followed by 6.9 ml of water. The suspension is filtered, the precipitate washed three times with 50 ml of hot methylene chloride, the combined filtrates dried, filtered and evaporated. The residue is taken up in acetone, the solution acidified with hydrogen chloride and diluted with diethyl ether, to yield the 4-benzyl-7,7-diphenyl-hexahydro-1,4-oxazepine hydrochloride melting at 243°-244°.

The mixture of 42.5 g thereof, 3.0 g of 10% of palladium on carbon and 750 ml of 95% aqueous ethanol is hydrogenated at 3 atmospheres and ambient temperature. After the theoretical amount of hydrogen has been absorbed, the mixture is filtered and the filtrate evaporated. The residue is partitioned between 200 ml of methylene chloride and 75 ml of 2N aqueous sodium hydroxide, the organic layer separated, washed with water, dried, filtered and evaporated. The residue is taken up in acetone and the solution acidified with cyclohexylsulfamic acid in acetone, to yield the 7,7-diphenyl-hexahydro-1,4-oxazepine cyclamate melting at 160°-162° (the regenerated free base melts at 72°-75°).

To the solution of 2.5 g of 7,7-diphenyl-hexahydro-1,4-oxazepine in 5 ml of dimethylformanide, 1.5 g of anhydrous potassium carbonate are added while stirring, followed by the dropwise addition of the solution of 0.85 g of chloroacetonitrile in 2 ml of dimethylformanide and the suspension is stirred for 5 hours at room temperature. It is poured onto a mixture of ice and water, the aqueous phase extracted twice with 20 ml of diethyl ether each, the extract dried, filtered and evaporated. The residue is recrystallized from ethanol, to yield the 4-cyanomethyl-7,7-diphenyl-hexahydro-1,4-oxazepine melting at 119°-121° (its hydrochloride melts at 178°-180° with decomposition).

7.4 g thereof are added in portions to the cooled, stirred suspension of 1.2 g of lithium aluminum hydride in 125 ml of anhydrous diethyl ether. The mixture is stirred at reflux for 10 hours, cooled in an ice-bath and 1.2 ml of water are added dropwise, followed by 1.2 ml aqueous sodium hydroxide and 3.6 ml water. The solids are filtered, washed with diethyl ether, the filtrate dried and evaporated to give the 4-(2-aminoethyl)-7,7-diphenyl-hexahydro-1,4-oxazepine melting at 75°-80° (it's dihydrochloride monohydrate melts at 230°-332° with decomposition).

EXAMPLE 2

In the exact analogous manner the following compounds of Formula I are prepared from equivalent amounts of the corresponding starting materials:

Ph = Ph' = phenyl, alk = alk' = ethylene

| No. | alk'' | A | Salt | m.p.° C (dec.) |
|---|---|---|---|---|
| 1 | (CH$_2$)$_3$ | (CH$_2$)$_3$ | HCl | 235-236 |
| 2 | " | CH$_2$—C(C$_2$H$_5$)$_2$—CH$_2$ | " | 236-238 |
| 3 | " | CH$_2$—C(nC$_4$H$_9$)$_2$—CH$_2$ | " | 194-196 |
| 4 | " | CH$_2$C(CH$_2$)$_4$—CH$_2$ | " | 247-249 |
| 5 | (CH$_2$)$_4$ |  | " | 156-158 |
| 6 | (CH$_2$)$_3$ | CH$_2$—C(CH$_2$)$_5$—CH$_2$ | " | 254-256 |
| 7 | " | 1,2,2-trimethyl-1,3-cyclopentylene | oxalate | 190-191 |
| 8 | " | 3,6-ethano-1,2-cyclohex-4-enylene | HCl | 248-250 |
| 9 | " | 1,2-phenylene | " | 149-150 |
| 10 | (CH$_2$)$_5$ | CH$_2$—C(CH$_2$)$_4$—CH$_2$ | " | 217-220 |
| 11 | (CH$_2$)$_7$ | " | " | 129-132 | i.e. the hydrochlorides of the N-[3-(7,7-diphenyl-hexahydro-1,4-oxazepin-4-yl)-propyl]-glutarimide the N-[3-(7,7-diphenyl-hexahydro-1,4-oxazepin-4-yl)-propyl]-β,β-(diethyl or di-n-butyl or tetramethylene)-glutarimides; the N-[4-(7,7-diphenyl-hexahydro-1,4-oxazepin-4-yl)-butyl]-β,β-tetramethylene-glutarimide; the N-[3-(7,7-diphenyl-hexahydro-1,4-oxazepin-4-yl)-propyl]β,β-pentamethylene-flutarimide; the oxalate of the N-[3-(7,7-diphenyl-hexahydro-1,4-oxazepin-4-yl)-propyl]-1,2,2-trimethyl-1,3-cyclopentane-dicarboximide and the hydrochlorides of the N-[3-(7,7-diphenyl-hexahydro-1,4-oxazepin-4-yl)-propyl]-3,6-ethano-1,2,3,6-tetrahydrophthalimide, the N-[3-(7,7-diphenyl-hexahydro-1,4-oxazepin-4-yl)-propyl]-phthalimide -oxazepin-4-yl)-pentyl or heptyl]-β,β-tetramethylene-glutarimides.

The starting material for said products is prepared as follows:

The solution of 22.2 g of 7,7-diphenyl-hexahydro-1,4-oxazepine and 0.2 g of hydroquinone in 50 ml of acrylonitrile is refluxed for 18 hours, cooled and evaporated. The residue is taken up in chloroform, the mixture filtered through a short column of silica gel, eluted with chloroform and the eluate evaporated. The residue is recrystallized from ethanol, to yield the 4-(2-cyanoethyl)-7,7-diphenyl-hexahydro-1,4-oxazepine melting at 106°-107°.

306 g thereof are added portionwise to the suspension prepared by combining the solution of 1.33 g of anhydrous aluminum chloride in 30 ml of diethyl ether with that of 0.38 g of lithium aluminum hydride in 30 ml of diethyl ether while stirring and cooling with an icebath. The mixture is allowed to warm up to room temperature, stirred for 5½ hours and cooled again to 0°-5°. Thereupon 5 ml of water and 15 ml of 3N aqueous sulfuric acid are added and the organic layer extracted with 3N aqueous sulfuric acid. The aqueous layers are combined, made basic with concentrated aqueous sodium hydroxide and the mixture extracted four times with 15 ml of diethyl ether each. The extract is dried, filtered and evaporated, to yield the 4-(3-aminopropyl)-7,7-diphenyl-hexahydro-1,4-oxazepine melting at 109°-114°.

The mixture of 4.6 g of 7,7-diphenyl-hexahydro-1,4-oxazepine, 1.88 g of 4-chlorobutyronitrile, 1.88 g of anhydrous sodium carbonate, 0.3 g of sodium iodide and 60 ml of 2-methyl-4-pentanone is stirred at reflux for 23 hours and evaporated. The residue is partitioned between diethyl ether and water, the ethereal solution separated, washed with saturated aqueous sodium chloride, dried and evaporated, to give the 4-(3-cyanopropy)-7,7-diphenyl-hexahydro-1,4-oxazepine melting at 89°-90°. (Analogously the 4-(4-cyanobutyl and 6-cyanohexyl)-7,7-diphenyl-hexahydro-1,4-oxazepines are prepared, melting at 67°-69° and showing an I.R. band at 2225cm$^{-1}$ respectively).

It is reduced as shown above, to yield the 4-(4-aminobutyl)-7,7-diphenyl-hexahydro-1,4-oxazepine melting at 110°-115°. The corresponding 4-(5-aminopentyl and 7-aminoheptyl)-7,7-diphenyl-hexahydro-1,4-oxazepine:dihydrochlorides melt at 166°-168° and 141°-143° respectively.

EXAMPLE 3

The mixture of 62 g of 4-(3-aminopropyl)-7,7-diphenyl-hexahydro-1,4-oxazepine, 33.6 g of β,β-tetramethylene-glutaric anhydride and 1.45 lt of xylene is stirred and heated to reflux. During the heating a solid intermediate separates and then redissolves as reflux temperature is reached with evolution of water. The liberated water is removed during the subsequent 5 hr. reflux period by means of a trap. On cooling, the solution is washed with 2N aqueous sodium hydroxide, then with saturated aqueous sodium chloride, dried and evaporated. The residue is dissolved in 400 ml of acetone and the solution stirred and maintained at room temperature during the addition of 52 ml of 3.45N ethereal hydrogen chloride. After stirring the resulting suspension at room temperature for 30 minutes, it is filtered, the residue washed successively with acetone and diethyl ether and air dried, to give the analytically pure N-[3-(7,7-diphenyl-hexahydro-1,4-oxazepine-4-yl)-propyl]-β,β-tetramethylene-glutarimide hydrochloride melting at 248°-250° with decomposition; it is identical with compound No. 4 of Example 2.

Analogously the N-[3-(7-(3-chlorophenyl)-7-phenyl-hexahydro-1,4-oxazepin-4-yl)-propyl]-β,β-tetramethylene-glutarimide hydrochloride, m.p. 231°-233° (dec.) and the N-[3-(7-phenyl-7-(3,4,5-thrimethoxyphenyl)-hexahydro-1,4-oxazepin-4-yl)-propyl]-β,β-tetramethylene-glutarimide hydrochloride, m.p. 168°-170° are prepared.

The starting material is prepared as follows: The solution of 650 ml of molar n-butyl lithium in hexane is diluted with 650 ml of dry tetrahydrofuran and the mixture stirred and cooled to −70° C under a nitrogen atmosphere. Then the solution of 37.2g of acetonitrile in 800 ml of tetrahydrofuran is added steadily over a period of 15 minutes. The resulting suspension is stirred at −70° C for 1 hour before the solution of 165 g of benzophenone in 800 ml of tetrahydrofuran is added steadily over 15 minutes. When addition is complete, the mixture is stirred without external cooling for 20 minutes, and then poured onto a mixture of 1.5 kg of crushed ice and 200 ml of 6N hydrochloric acid. The organic layer is separated and the aqueous solution extracted with diethyl ether. The combined organic solutions are dried and evaporated to give the β-hydroxy-β,β-diphenyl-propionitrile melting at 135°-8°.

197 g thereof are powdered and added in portions over a 105 minute period to the stirred suspension of 65 g of lithium aluminum hydride in 4.4 lt of dry diethyl ether being externally cooled with tap-water. The suspension is stirred at room temperature for 15 hours and finally at reflux for 3 hours. It is cooled with ice and 65 ml of water, 65 ml of 15% aqueous sodium hydroxide and 195 ml of water are added dropwise. The mixture is filtered, the solids washed with chloroform, the filtrate dried and evaporated to give the 3-hydroxy-3,3-diphenyl-propylamine melting at 140°-143°.

To the suspension of 373 g thereof in 195 g of pyridine and 15 lt of methylene chloride, the solution of 241 g of benzoyl chloride in 1.8 lt of methylene chloride is added dropwise during 2 hours while stirring and cooling with ice. When addition is complete the solution is stirred for an additional hour at 0°-5° and is then washed successively with 1 lt of N hydrochloric acid, 1 lt of N aqueous sodium hydroxide and 1 lt of water, dried and evaporated, to give the N-benzoyl-3-hydroxy-3,3-diphenyl-propylamine melting at 152°-154°.

411 g thereof are added in portions over 2 hours to the well stirred, ice cooled suspension of 100 g of lithium aluminum hydride in 1 lt of dry diethyl ether. The mixture is stirred without cooling for 2 hours, and under reflux for another 3 hours. It is cooled with ice and 100 ml of water, 100 ml of 15% aqueous sodium hydroxide and 100 ml of water are added dropwise. The mixture is filtered and the sllids are extracted with warm chloroform. The filtrate is dried and evaporated, to give the N-benzyl-3-hydroxy-3,3-diphenyl-propylamine melting at 148°-150°.

To the solution of 120 g thereof in 44.2 g of chloroacetyl chloride in 400 ml of methylene chloride is added dropwise while stirring and cooling with ice. After stirring at 0°-5° for 45 minutes, the solution is washed successively with N hydrochloric acid and 10% aqueous sodium carbonate dried and evaporated. The residue solidifies on standing and is triturated with cold diethyl ether to afford the N-benzyl-N-chloroacetyl-3-hydroxy-3,3-diphenyl-propylamine melting at 92°-94°.

149 g thereof are dissolved in 650 ml of dry dimethyl formamide and the solution is distilled at 1 mmHg-pressure until 50-70 ml of dimethylformamide have been collected. The solution is added dropwise to the stirred suspension of 9.6 g of oil-free sodium hydride in 150 ml of dry dimethylformamide. The temperature is maintained at 30°-35° by intermittent cooling during the addition, whereupon the mixture is stirred at room temperature for 15 hours. It is evaporated at 1 mmHg pressure, the residue taken up in 1 lt of methylene chloride and the solution washed successively with 0.1N hydrochloric acid and water, dried and evaporated. The residue is triturated with diethyl ether to give the 4-benzyl-7,7-diphenyl-hexahydro-1,4-oxazepin-3-one melting at 186°–188°.

100 g thereof are added in portions to the stirred, ice-cooled suspension of 12.7 g of lithium aluminum hydride in 2 lt of dry diethyl ether and the mixture is stirred and allowed to reach room temperature. It is stirred and refluxed for 10 hours, then cooled with ice and 12.7 ml of water, 12.7 ml of 15% aqueous sodium hydroxide and 38 ml of water are added dropwise. After filtration, the solids are extracted with warm chloroform and the filtrate is dried and evaporated to give the 4-benzyl-7,7-diphenyl-hexahydro-1,4-oxazepine melting at 129°–131°.

The mixture of 20 g thereof, 2 g of 10% palladium on carbon and 210 ml of 95% ethanol containing 2.15 g of hydrochloric acid is hydrogenated at 3 atm. and 50° for 6 hours. The catalyst is filtered off and the filtrate evaporated. The residue is triturated with diethyl ether, filtered off and taken up in methylene chloride. The solution is washed with aqueous sodium hydroxide, dried and evaporated, to yield the 7,7-diphenyl-hexahydro-1,4-oxazepine melting at 72°–75°.

60 g thereof are added portionwise to 200 ml of acrylonitrile and the solution is stirred overnight at room temperature. It is evaporated, and the solid residue air dried, to yield the 4-(2-cyanoethyl)-7,7-diphenyl-hexahydro-1,4-oxazepine melting at 105°–107°.

63 g thereof are added portionwise to the suspension of 11 g of lithium aluminum hydride in 2 lt of anhydrous diethyl ether and the mixture is stirred at 0° for 15 minutes. It is stirred and allowed to reach room temperature during an additional 30 minutes and is then refluxed for 12 hours. On cooling with ice 11 ml of water, 11 ml of 15% aqueous sodium hydroxide and 33 ml of water are added, the resulting suspension is filtered, the solids washed with diethyl ether, the filtrate dried and evaporated to give the 4-(3-aminopropyl)-7,7-diphenyl-hexahydro-1,4-oxazepine melting at 68°–70°.

In the analogous manner the 4-(3-aminopropyl)-7-(3-chlorophenyl and 3,4,5-trimethoxyphenyl)-7-phenyl-hexahydro-1,4-oxazepines are prepared, the dihydrochlorides of which melt at 123°–126° (dec.) and 149°–152° (dec.) respectively; and their cyanoprecursors show an I.R. band at 2250cm⁻¹, and melt at 113°–115° respectively.

EXAMPLE 4

2.35 g of solid β,β-tetramethylene-glutaric anhydride are added all at once to the stirred solution of 5.1 g of 4-(7-aminoheptyl)-7,7-diphenyl-hexahydro-1,4-oxazepine in 100 ml of xylene, the resulting suspension is stirred at reflux for 4 hours and the liberated water collected in a water trap. The cooled solution is filtered and the solid is washed with diethyl ether and dried to give residue A melting at 124°–126°. The filtrate is washed with 2N aqueous sodium hydroxide and brine, dried and evaported. The residue B is taken up in acetone and the solution acidified with ethereal hydrogen chloride, to yield the N-[7-(7,7-diphenyl-hexahydro-1,4-oxazepin-4-yl)-heptyl]-β,β-tetramethylene-glutarimide hydrochloride melting at 129°–132° with decomposition.

Residue A is the corresponding ring-open amide of the formula

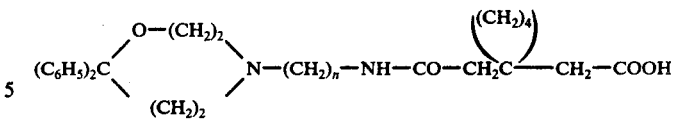

(n=7), which can be converted into residue B merely by heating 1 g thereof in 20 ml of xylene under reflux with provision of a water trap to remove the liberated water.

The analogously obtained ring-open byproduct (n=3) of the compound of Example 3 melts at 176°–178° with decomposition.

EXAMPLE 5

Preparation of 10,000 tablets each containing 50.0 mg of the active ingredient:

| Formula: | |
|---|---|
| N-[3-(7,7-diphenyl-hexahydro-1,4-oxazepin-4-yl)-propyl]-β,β-tetramethylene-glutarimide hydrochloride | 500.00 g |
| Lactose | 1,706.00 g |
| Corn Starch | 90.00 g |
| Polyethylene glycol 6,000 | 90.00 g |
| Talcum powder | 90.00 g |
| Magnesium stearate | 24.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concabe punches with 7.1 mm diameter, uppers bisected.

Analogously tablets of the other compounds of the invention are prepared, preferably of those corresponding to Formula II and being illustrated by the previous examples.

I claim:

1. An N-(7,7-diphenyl-hexahydro-1,4-oxazepin-4-yl-alkyl)-dicarboximide corresponding to the formula

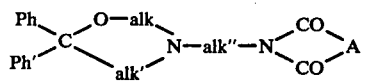

wherein each of alk and alk' is lower alkylene separating the adjacent atoms by 2 carbon atoms, alk" is lower alkylene separating the adjacent atoms by at least 2 carbon atoms, each of Ph and Ph' is phenyl, unsubstituted or substituted by up to three members of lower alkyl, lower alkoxy, lower alkylmercapto, hydroxy, halogeno or trifluoromethyl, and A is lower alkylene, lower alkenylene, 5 to 7 ring-membered mono- or bicyclic 1,2- or 1,3-(cycloalkylene or cycloalkenylene), 5 to 7 ring-membered spirocycloalkane-lower alkylene or 1,2-phenylene, said mono- or bicyclic 1, 2- or 1,3-(cycloalkylene or cycloalkenylene) are unsubstituted or substituted by up to three lower alkyls, and said 1,2-phenylene radical is substituted in the same manner as Ph, or a therapeutically acceptable acid addition salt thereof.

2. A compound as claimed in claim 1, in which formula each of alk and alk' is lower alkylene separating the adjacent atoms by 2 carbon atoms, alk" is lower alkylene separating the adjacent atoms by at least 2 carbon atoms, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, and A is lower alkylene, lower alkenylene, 5 to 7 ring-memberd mono- or bicyclic 1,2- or 1,3-(cycloalkylene or cycloalkenylene), 5 to 7 ring-membered 2-spirocycloalkane-1,3- propylene, 1,2-phenylene, (lower alkyl, lower alkoxy, lower alkylmercapto, hydroxy, halogeno or trifluoromethyl)-1,2-phenylene, or a therapeutically acceptable acid addition salt thereof.

3. A compound as claimed in claim 1, in which formula each of alk and alk' is ethylene or 1,2-propylene, alk" is ethylene, 1,3-propylene or 1,4-butylene, each of Ph and Ph' is phenyl or (lower alkyl)-phenyl, and A is ethylene, 1,3-propylene, 2,2-di-(methyl, ethyl, n-proply or n-butyl)-1,3-propylene, 1,4-butylene or 1,4-but-2-enylene, 1,2- or 1,3-cyclopentylene or cyclohexylene, 1,2,2-trimethyl-1,3-cyclopentylene, 2-methyl-1,3-cyclohexylene, 3,6-ethano-1,2-cyclohexylene or -cyclo-4-hexenylene, 2-spirocyclopentane or --hexane-1,3-propylene, 1,2-phenylene or (lower alkyl)-1,2-phenylene, or a therapeutically acceptable acid addition salt thereof.

4. A compound as claimed in claim 1 and corresponding to the formula

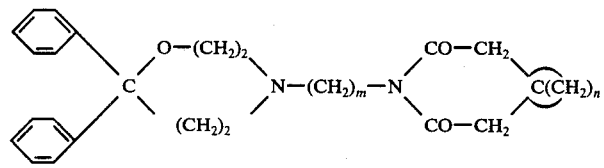

wherein $m$ is an integer from 2 to 4 and n such from 4 to 5, or a therapeutically acceptable acid addition salt thereof.

5. A compound as claimed in claim 4, in which formula $m$ is 3 or 4 and n is four, or a therapeutically acceptable acid addition salt thereof.

6. A compound as claimed in claim 5 and being the N-[3-(7,7-diphenyl-hexahydro-1,4-oxazepin-4-yl)-propyl]-$\beta,\beta$-tetramethylene-glutarimide, or a therapeutically acceptable acid addition salt thereof.

7. A phamaceutical composition for treating asthmatic, allergic and inflammatory conditions in mammals comprising a pharmacologically effective amount of a compound as claimed in claim 1, together with a pharmaceutical excipient.

8. A method of treating asthmatic, allergic and inflammatory conditions in mammals, which consists in administering to said mammals enterally or parenterally a composition as claimed in claim 7.

* * * * *